(12) United States Patent
Labaer et al.

(10) Patent No.: US 11,124,791 B2
(45) Date of Patent: Sep. 21, 2021

(54) GENERATING RECOMBINANT AFFINITY REAGENTS WITH ARRAYED TARGETS

(71) Applicants: ARIZONA BOARD OF REGENTS ON BEHALF OF ARIZONA STATE UNIVERSITY, Scottsdale, AZ (US); THE BOARD OF TRUSTEES OF THE UNIVERSITY OF ILLINOIS, Urbana, IL (US)

(72) Inventors: Joshua Labaer, Chandler, AZ (US); Kevin Gorman, Chicago, IL (US); Brian Kay, Chicago, IL (US); Jie Wang, Tempe, AZ (US); Ji Qiu, Chandler, AZ (US)

(73) Assignees: ARIZONA BOARD OF REGENTS ON BEHALF OF ARIZONA STATE UNIVERSITY, Scottsdale, AZ (US); THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 15/748,946

(22) PCT Filed: Sep. 13, 2016

(86) PCT No.: PCT/US2016/051514
§ 371 (c)(1),
(2) Date: Jan. 30, 2018

(87) PCT Pub. No.: WO2017/048709
PCT Pub. Date: Mar. 23, 2017

(65) Prior Publication Data
US 2019/0062728 A1 Feb. 28, 2019

Related U.S. Application Data

(60) Provisional application No. 62/218,362, filed on Sep. 14, 2015.

(51) Int. Cl.
*C40B 30/04* (2006.01)
*C12N 15/10* (2006.01)
*C12Q 1/6811* (2018.01)

(52) U.S. Cl.
CPC ..... *C12N 15/1037* (2013.01); *C12N 15/1041* (2013.01); *C12N 15/1062* (2013.01); *C12Q 1/6811* (2013.01); *C40B 30/04* (2013.01)

(58) Field of Classification Search
None
See application file for complete search history.

(56) References Cited

U.S. PATENT DOCUMENTS 6,818,418 B1   11/2004   Lipovsek
8,278,419 B2   10/2012   Jacobs
(Continued)

FOREIGN PATENT DOCUMENTS

DK   WO-2006/053571 A2 *   5/2006   ............. C40B 50/06
WO   2006053571 A2   5/2006
(Continued)

OTHER PUBLICATIONS

Amiss, Terry J., et al. "Engineering and rapid selection of a low-affinity glucose/galactose-binding protein for a glucose biosensor." Protein Science 16.11 (2007): 2350-2359.
(Continued)

*Primary Examiner* — Christian C Boesen
(74) *Attorney, Agent, or Firm* — Quarles & Brady LLP

(57) ABSTRACT

Methods for screening of affinity reagents for many target proteins of interest simultaneously. Arrayed targets (e.g., peptide, protein, RNA, cell, etc.) are used in affinity selection experiments to reduce the amount of target needed and to improve the throughput of discovering recombinant affinity reagents to a large collection of targets.

6 Claims, 5 Drawing Sheets

(56) References Cited

U.S. PATENT DOCUMENTS

| | | | |
|---|---|---|---|
| 9,442,111 | B2 | 9/2016 | Lindsay |
| 9,535,070 | B2 | 1/2017 | Saul |
| 9,719,144 | B2 | 8/2017 | Rajmalnik-Brown |
| 9,857,374 | B2 | 1/2018 | Labaer |
| 9,938,523 | B2 | 4/2018 | Labaer |
| 10,045,990 | B2 | 8/2018 | Festa |
| 10,351,842 | B2 | 7/2019 | Labaer |
| 2012/0003639 | A1* | 1/2012 | Kerlikowske .... G01N 33/57415 435/6.11 |
| 2014/0162902 | A1 | 6/2014 | Labaer |
| 2014/0371091 | A1 | 12/2014 | Wiktor |
| 2015/0362497 | A1 | 12/2015 | Anderson |
| 2016/0041159 | A1 | 2/2016 | Labaer |
| 2016/0083793 | A1 | 3/2016 | Labaer |
| 2016/0195546 | A1 | 7/2016 | Labaer |
| 2017/0045515 | A1 | 2/2017 | Anderson |
| 2017/0115299 | A1 | 4/2017 | Saul |
| 2017/0176423 | A1 | 6/2017 | Anderson |
| 2017/0356029 | A1 | 12/2017 | Krajmalnik-Brown |
| 2017/0363631 | A1 | 12/2017 | Labaer |
| 2018/0067117 | A1 | 3/2018 | Labaer |
| 2018/0201923 | A1 | 7/2018 | Labaer |
| 2018/0224448 | A1 | 8/2018 | Wang |
| 2018/0267029 | A1 | 9/2018 | Wiktor |
| 2018/0320230 | A1 | 11/2018 | Labaer |
| 2019/0004051 | A1 | 1/2019 | Labaer |
| 2019/0127778 | A1 | 5/2019 | Labaer |
| 2019/0144923 | A1 | 5/2019 | Krajmalnik-Brown |
| 2019/0162725 | A1 | 5/2019 | Magee |
| 2019/0302122 | A1 | 10/2019 | Katchman et al. |
| 2019/0366237 | A1 | 12/2019 | LaBaer |

FOREIGN PATENT DOCUMENTS

| | | |
|---|---|---|
| WO | 2009085462 A2 | 7/2009 |
| WO | 2011130324 A1 | 10/2011 |
| WO | 2012021887 A2 | 2/2012 |
| WO | 2013019680 A1 | 2/2013 |
| WO | 2013063126 A2 | 5/2013 |
| WO | 2013090364 A1 | 6/2013 |
| WO | 2013176774 A9 | 11/2013 |
| WO | 2014120902 A1 | 8/2014 |
| WO | 2014143954 A2 | 9/2014 |
| WO | 2014145458 A1 | 9/2014 |
| WO | 2015148202 A1 | 10/2015 |
| WO | 2015167678 A1 | 11/2015 |
| WO | 2015175755 A1 | 11/2015 |
| WO | 2016094558 A1 | 6/2016 |
| WO | 2016141044 A1 | 9/2016 |
| WO | 2017075141 A1 | 5/2017 |
| WO | 2017123648 A1 | 7/2017 |
| WO | 2017218677 A2 | 12/2017 |
| WO | 2018013531 A1 | 1/2018 |
| WO | 2018156553 A1 | 8/2018 |
| WO | 2019136169 A1 | 7/2019 |

OTHER PUBLICATIONS

Binkowski B et al. "Correcting errors in synthetic DNA through consensus shuffling." Nucleic Acids Res. 2005, 33, e55.

Bloom L et al. "FN3: A new protein scaffold reaches the clinic." Drug Discov. Today 2009, 14, 949-955.

Bradbury A et al. "Beyond natural antibodies: The power of in vitro display technologies." Nat. Biotechnol. 2011, 29, 245-254.

Cadwell R et al. "Mutagenic PCR." Genome Res. 1994, 3, S136-S140.

Detanico T et al. "Somatic mutagenesis in autoimmunity." Autoimmunity 2013, 46, 102-114.

Dreier, B. and A. Pluckthun, Ribosome display: a technology for selecting and evolving proteins from large libraries. Methods Mol Biol, 2011. 687: p. 283-306.

Duan J et al. "Fibronectin type III domain based monobody with high avidity." Biochemistry 2007, 46, 12656-12664.

Fukuda I et al. "In vitro evolution of single-chain antibodies using mRNA display." Nucleic Acids Res. 2006, 34, e127.

Grebien F et al. "Targeting the SH2-kinase interface in Bcr-Abl inhibits leukemogenesis." Cell 2011, 147, 306-319.

Hackel B et al. "Picomolar affinity fibronectin domains engineered utilizing loop length diversity, recursive mutagenesis, and loop shuffling." J. Mol. Biol. 2008, 381, 1238-1252.

Holland E et al. "AXM mutagenesis: An efficient means for the production of libraries for directed evolution of proteins." J. Immunol. Methods 2013, 394, 55-61.

Holland E et al. "In vivo elimination of parental clones in general and site-directed mutagenesis." J. Immunol. Methods 2015, 417, 67-75.

Huang R et al. "Improvements to the Kunkel mutagenesis protocol for constructing primary and secondary phage-display libraries." Methods. 2012, 58, 10-17.

Huang R et al. "Streamlining the Pipeline for Generation of Recombinant Affinity Reagents by Integrating the Affinity Maturation Step" Int. J. Mol. Sci. 2015, 16, 23587-23603.

Huovinen T et al. "Primer extension mutagenesis powered by selective rolling circle amplification." PLoS ONE 2012, 7, e31817.

International Searching Authority, International Search Report and Written Opinion for PCT/US16/51514, dated Dec. 1, 2016, 6 pages.

Jermutus L et al. "Tailoring in vitro evolution for protein affinity or stability." Proc. Natl. Acad. Sci. USA 2001, 98, 75-80.

Karthikeyan K, et al. A Contra Capture Protein Array Plafform for Studying Post-translationally Modified (PTM) Auto-antigenomes. Mol Cell Proteomics. Jul. 2016;15(7):2324-37. doi: 10.1074/mcp.M115.057661. Epub May 2, 2016. PubMed PMID: 27141097; PubMed Central PMCID: PMC4937507.

Kehoe, J.W. et al, Filamentous phage display in the new millennium. Chem Rev, 2005. 105(11): p. 4056-4072.

Koide A et al. "High-affinity single-domain binding proteins with a binary-code interface." Proc. Natl. Acad. Sci. USA 2007, 104, 6632-6637.

Koide A et al. "Teaching an old scaffold new tricks: Monobodies constructed using alternative surfaces of the FN3 scaffold." J. Mol. Biol. 2012, 415, 393-405.

Kunkel T. "Rapid and efficient site-specific mutagenesis without phenotypic selection" Proc. Natl. Acad. Sci. USA 1985, 82, 488-492.

Miersch, S. and J.LaBaer, Nucleic Acid programmable protein arrays: versatile tools for array-based functional protein studies. Curr Protoc Protein Sci, 2011. Chapter 27: p. Unit27 2.

Olson C et al. "mRNA display selection of a high-affinity, modification-specific phospho-IkBa-binding fibronectin." ACS Chem. Biol. 2008, 3, 480-485.

Parker M et al. "Antibody mimics based on human fibronectin type three domain engineered for thermostability and high-affinity binding to vascular endothelial growth factor receptor two." Protein Eng. Des. Sel. 2005, 18, 435-444.

Poulsen T et al. "Limits for antibody affinity maturation and repertoire diversification in hypervaccinated humans." J. Immunol. 2011, 187, 4229-4235.

Seelig, B., mRNA display for the selection and evolution of enzymes from in vitrotranslated protein libraries. Nat Protoc, 2011. 6(4): p. 540-552.

Stemmer W. "DNA shuffling by random fragmentation and reassembly: In vitro recombination for molecular evolution." Proc. Natl. Acad. Sci. USA 1994, 91, 10747-10751.

Thie H et al. Affinity maturation by phage display. Methods Mol. Biol. 2009, 525, 309-322.

Willuda J et al. "High thermal stability is essential for tumor targeting of antibody fragments: Engineering of a humanized anti-epithelial glycoprotein-2 (epithelial cell adhesion molecule) single-chain Fv fragment." Cancer Res. 1999, 59, 5758-5767.

Wojcik J et al. "A potent and highly specific FN3 monobody inhibitor of the abl SH2 domain." Nat. Struct. Mol. Biol. 2010, 17, 519-527.

Zaccolo M et al. "An approach to random mutagenesis of DNA using mixtures of triphosphate derivatives of nucleoside analogues." J. Mol. Biol. 1996, 255, 589-603.

(56) References Cited

OTHER PUBLICATIONS

Zahnd C et al. "Computational analysis of off-rate selection experiments to optimize affinity maturation by directed evolution." Protein Eng. Des. Sel. 2010, 23, 175-184.
U.S. Appl. No. 16/097,791, filed Oct. 30, 2018, LaBaer et al.

* cited by examiner

GENERATING RECOMBINANT AFFINITY REAGENTS WITH ARRAYED TARGETS

CROSS-REFERENCE TO RELATED APPLICATIONS

This application represents the U.S. National Stage entry of International Application No. PCT/US2016/051514, filed on Sep. 13, 2016, and claims priority to and the benefit of U.S. Provisional Application No. 62/218,362, filed on Sep. 14, 2015, the disclosures of which are incorporated herein by reference.

STATEMENT REGARDING FEDERALLY SPONSORED RESEARCH

This invention was made with government support under grant number DK093444, awarded by the National Institutes of Health. The government has certain rights in this invention.

FIELD OF THE INVENTION

Embodiments herein relate generally to the field of high-throughput screening of affinity reagents for many targets of interest simultaneously.

BACKGROUND OF THE INVENTION

Affinity selection is a process that utilizes so-called "display technologies" (ribosome-, mRNA-, and phage-display) to isolate recombinant affinity reagents for a given target (e.g., peptide, protein, RNA, cell, etc.). One of the bottlenecks of this process is producing the targets that are needed for the affinity selection.

In fact, many affinity reagent pipelines devote a significant amount of resources to generating high-quality target proteins. In addition, because the targets used in selection are sometimes labile (i.e., they are prone to degradation and denaturation), affinity selections fail.

Consequently, achieving a high-throughput and efficient affinity selection process remains problematic.

SUMMARY OF THE INVENTION

Embodiments herein relate to cost-effective screening of affinity reagents for many target proteins of interest simultaneously. Consequently, affinity reagents can be discovered that will potentially aid in detecting, inhibiting, or activating target proteins.

In various embodiments, arrayed targets (e.g., peptide, protein, RNA, cell, etc.) are used in affinity selection experiments to reduce the amount of target needed and to improve the throughput of discovering recombinant affinity reagents to a large collection of targets.

Preferably, protein-target method embodiments herein use arrayed material that is translated shortly before each round of selection, as using labile protein targets is found to be less effective than using freshly made target samples.

These and other aspects of the embodiments disclosed herein will be apparent upon reference to the following disclosure.

DETAILED DESCRIPTION OF THE INVENTION

Embodiments herein relate to arrayed targets that are used in affinity selection of display libraries. Traditionally, affinity selection procedures use individual protein or peptide as targets, which have a low throughput (i.e., one at a time) and require a significant amount of target.

With the advent of so-called "array" technologies, one is able to a) spot proteins or peptides on an array or b) synthesize in situ thousands of fresh target proteins on a solid surface (array) within a few hours. Thus, one solution to the low-throughput/large amount of target limitations is to affinity select with arrayed targets. For example, synthetic peptides or proteins can be spotted or captured in arrays on glass slides. Alternatively, proteins can be synthesized in situ in individual spots of an array. The method of choice of in vitro synthesis and capture of proteins in spots is the nucleic-acid programmable protein array (NAPPA).

In NAPPA, cDNAs coding for the target of interest are cloned into an expression vector, which generates a fusion (Halo Tag, GST, etc.) to the target, and spotted onto an aminosilane-coated glass slide. Then to each spot, a HeLa cell in vitro transcription-translation reagent is added, whereby the fusion gene is transcribed into mRNA and translated. The nascent proteins are captured to the slide with an antibody/affinity agent to the fusion partner (i.e., HaloTag-ligand, α-GST antibody) that is spotted adjacent to the DNA during the manufacture of the array. This method allows for up to thousands of protein targets to be arrayed.

Figure 1:
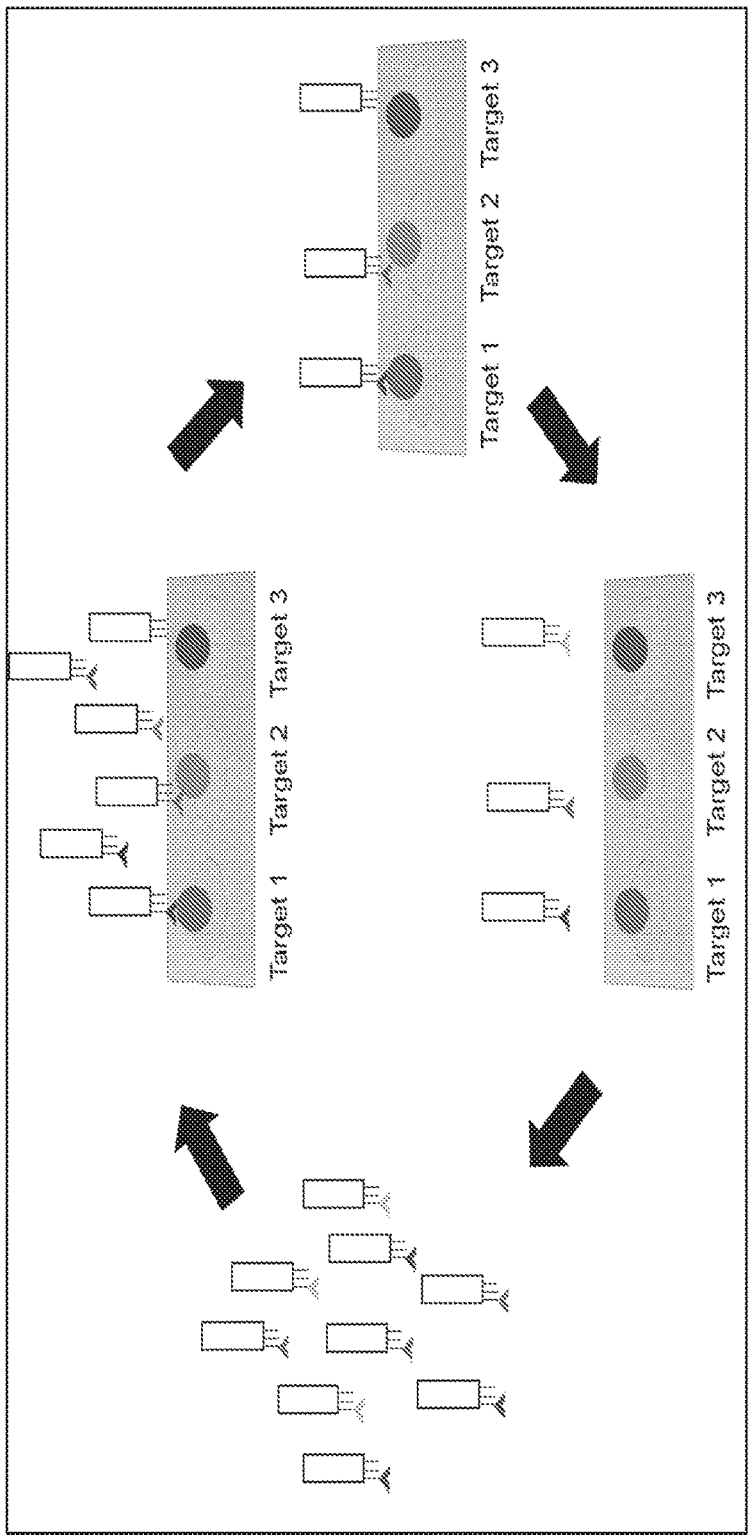
FIG. 1. Affinity selection via phage-display using arrayed targets. First, the naïve library is incubated with freshly-translated target on the array. Next a wash step removes non-binding clones from the array, while binding clones are retained. Phage particles remaining on the array are then eluted from their respective targets and are amplified for subsequent rounds.

In the embodiments disclosed herein, targets, which have been generated by NAPPA, are used in affinity selection experiments (FIG. 1). By using freshly translated protein/peptide targets (i.e., within approximately 1 to 24 hours), the likelihood of denaturation of targets during storage and freeze thawing is reduced.

In addition, this process is performed on an array, which can produce many fresh protein samples. Therefore, one is able to perform a multiplexed selection on multiple targets using a single library, thereby reducing the time and cost of generating these reagents.

Figure 2:
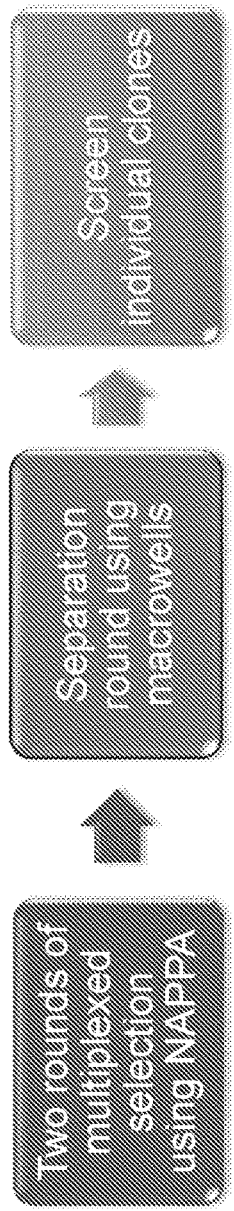
FIG. 2. Proposed pipeline for identifying recombinant affinity reagents.

In some method embodiments, the process includes first performing two rounds of multiplexed panning on the array, followed by a separation round using a macrowell format (that still utilizes freshly-translated target protein), which separates binding phage based on their cognate target (FIG. 2). Finally, the resulting clones from pools isolated in the separation round are analyzed via macrowell analysis or ELISA to identify clones with the highest affinity for the target.

Figure 3:
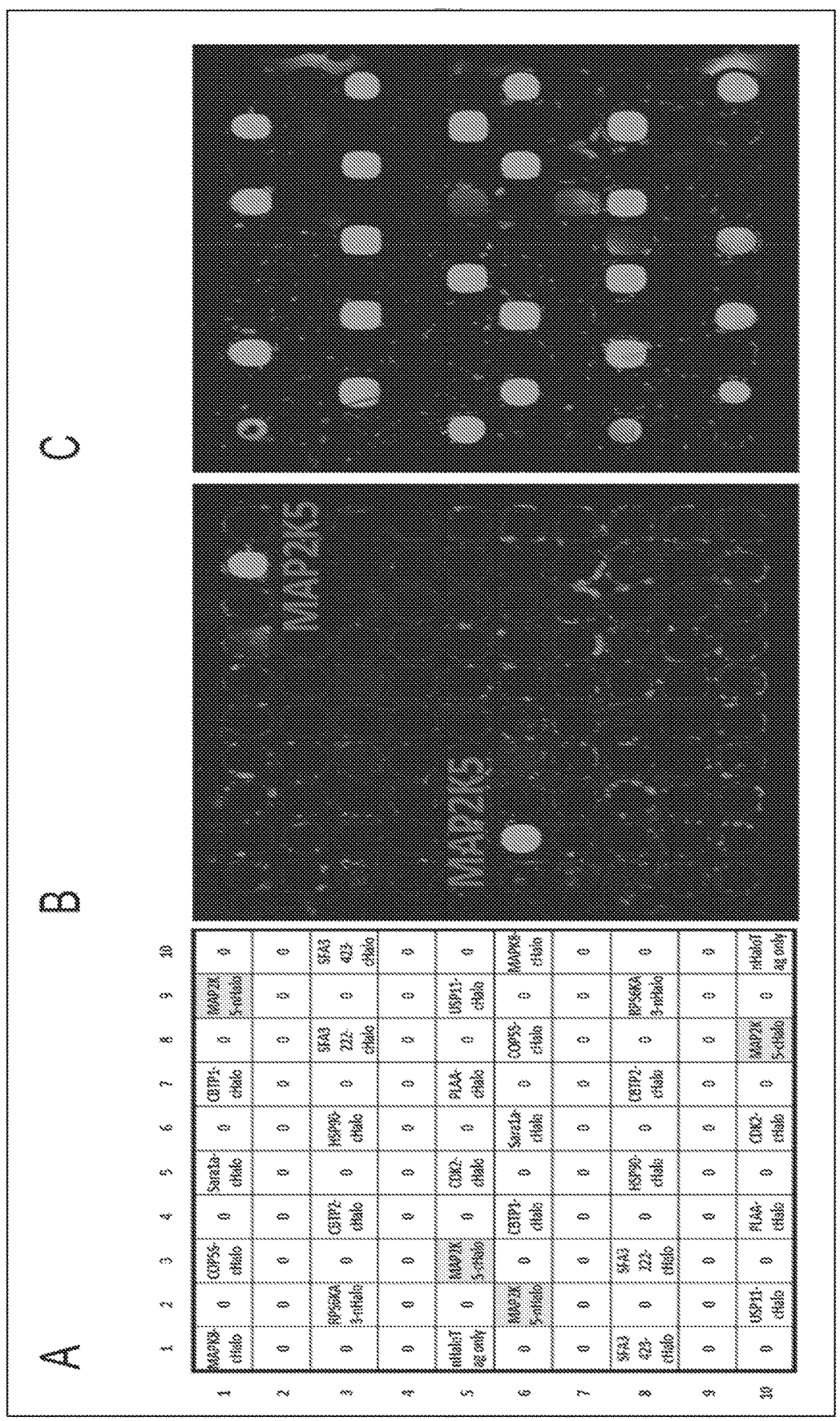
FIG. 3. Detecting phage particles on NAPPA array. (A) Schematic of array layout containing 13 unique targets. (B) Detection of phage particles (1:1000) displaying a known MAP2K5 binder. (C) Detection of freshly-translated protein in wells via the halo epitope.
Figure 4:
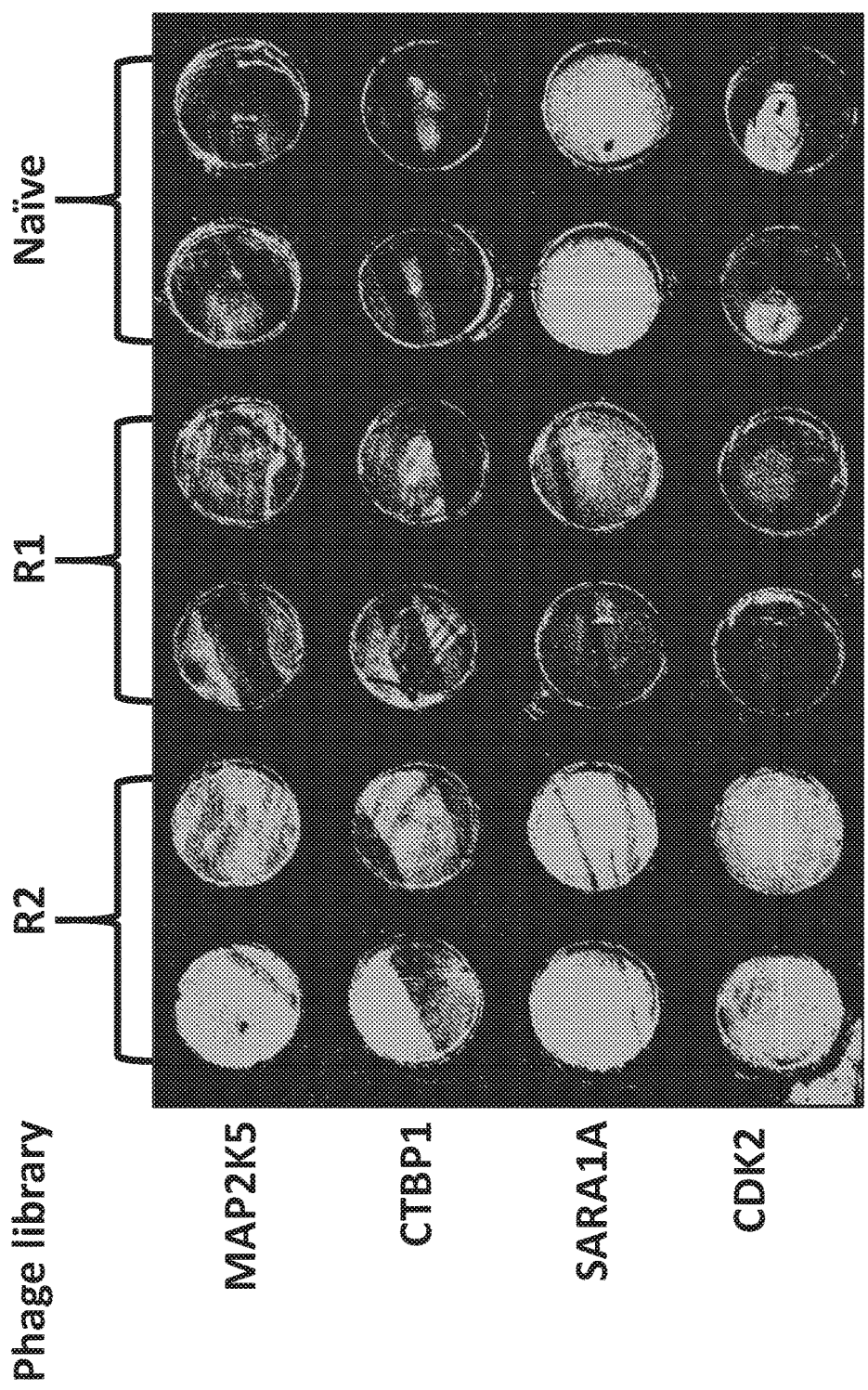
FIG. 4. Phage library affinity selection of the protein targets MAP2K5, CTBP1, SARA1A, and CDK2. Phage Input is normalized by counting colonies of TG1 cells infected by each library. Approximately, R1-lib:R2-Lib:Naïve Lib=1:1:10.
Figure 5:
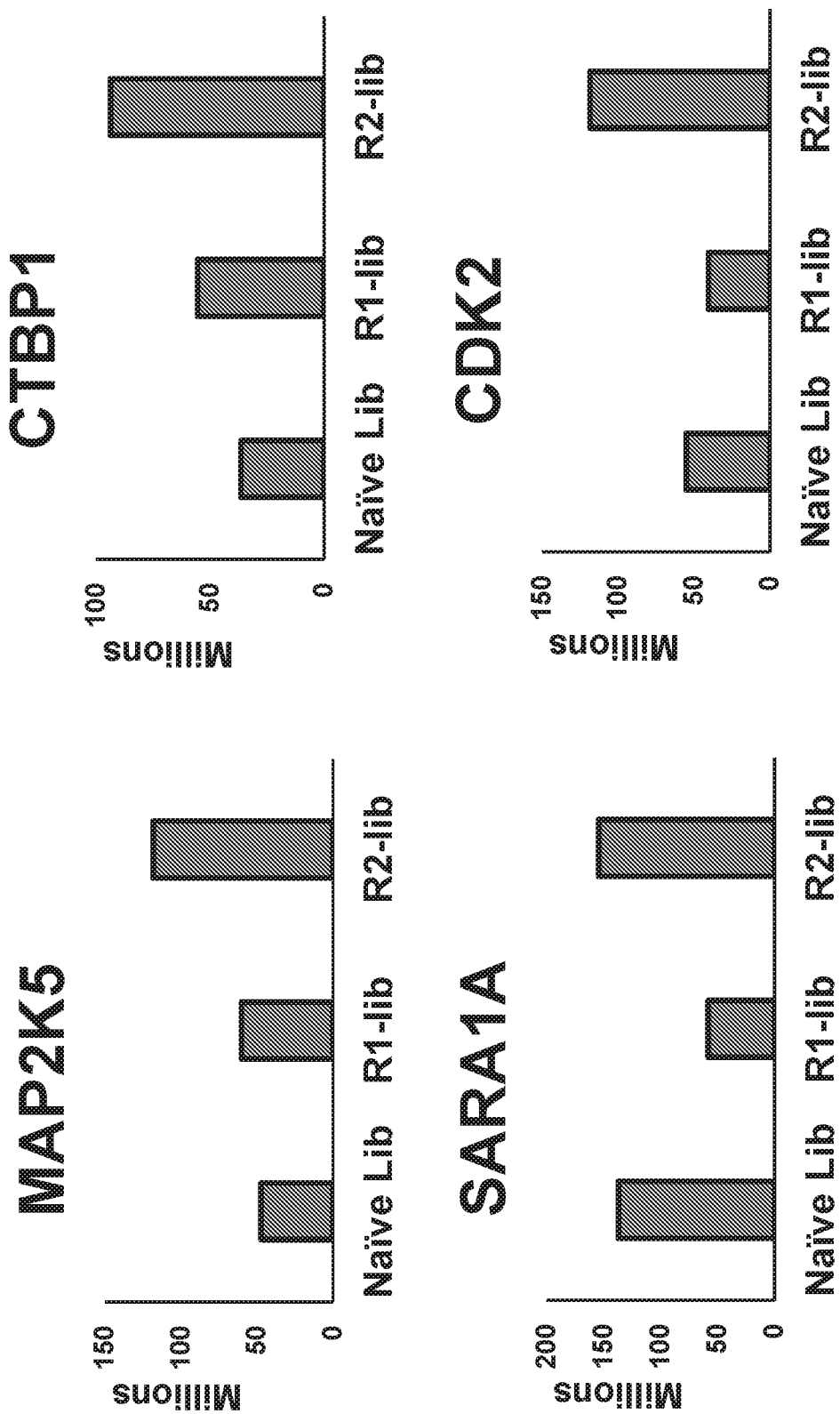
FIG. 5. Graphs of colony counts for the naive library, Round 1, and Round 2 of selection for the protein targets of the experiment in FIG. 4.
Figure 6:
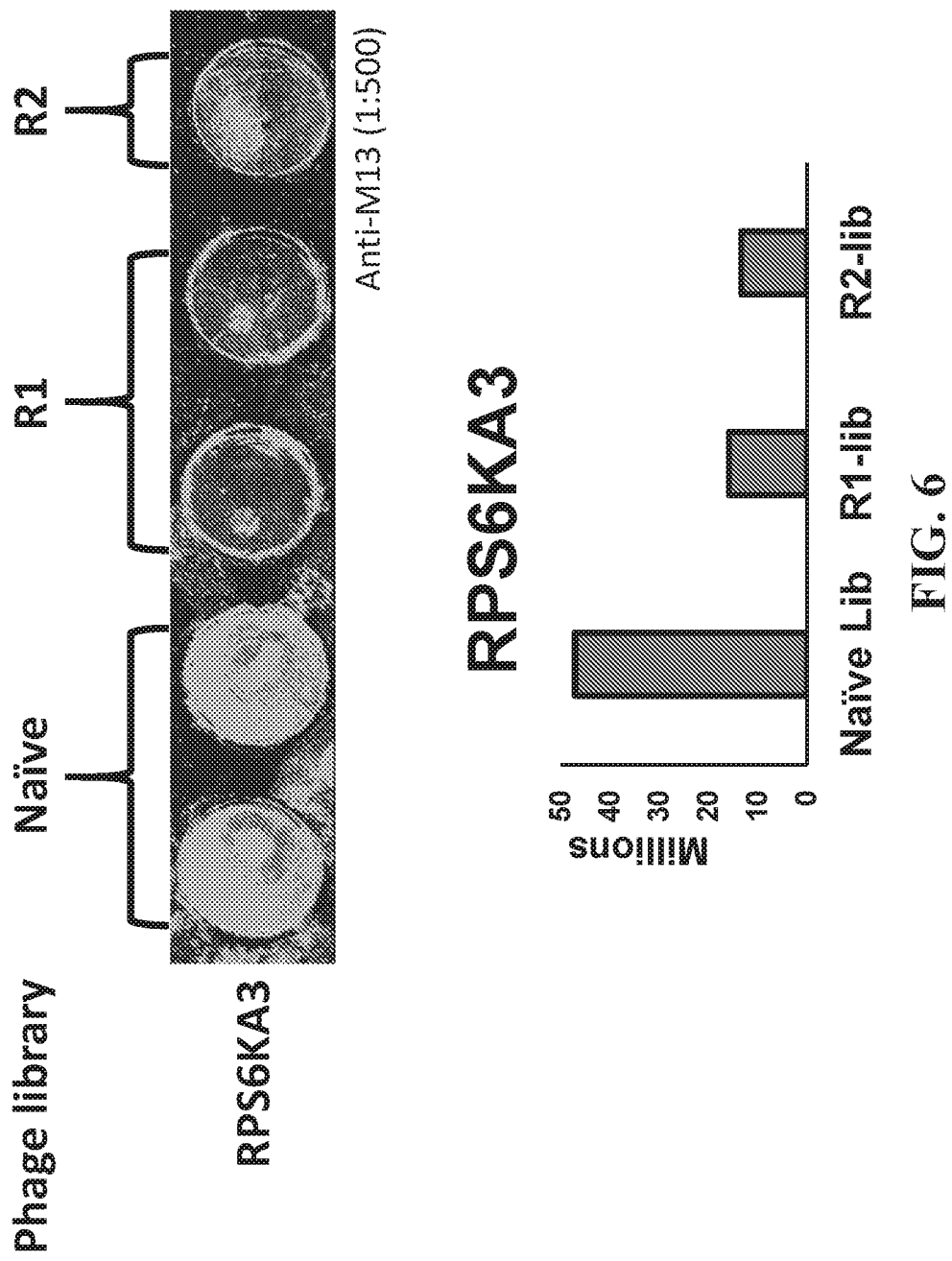
FIG. 6. RPS6KA3 is an antigen that is not selected in the initial enrichment experiment. Therefore, we would not expect increased signal after two rounds of enrichment. Consistently, this data shows RPS6KA3 was negatively selected.

Recently, we have shown that an M13 bacteriophage, which displays a known binder to a particular protein target, can be detected to bind the NAPPA-generated and arrayed form of the same target (FIG. 3). A strong signal occurs when the virions are either pure or mixed 1 to 100 with a phage library containing $2\times10^{10}$ members. This finding demonstrates that virions displaying a binder can bind selectively and efficiently to a NAPPA-generated target protein.

EXAMPLES

One Construction and Array Production

All genes of interest were cloned in pJFT7_nHALO or pJFT7_cHALO, the NAPPA compatible expression vectors. These expression vectors allow the in vitro expression of proteins of interest with a terminal HaloTag. Protein arrays were constructed through a contra capture concept as described (1).

Enrichment

Array displaying MAP2K5, CTBP1, SARA1A and CDK2 were constructed and expressed. Initial non-enrichment phage library was incubated and washed to allow binding. Mild acid (0.2M Glycine pH2.0) wash was used to remove the bond phage particles and immediately neutralized using 1M Tris-Cl (pH9.1). *E. coli* were then infected with the collected phage for titring and amplification as previously described (2).

Probe Libraries on Arrays

To evaluate the enrichment efficiency, same input of non-enriched library, R1 and R2 were probed on the protein microarray containing MAP2K5, CTBP1, SARA1A, CDK2 and RPS6KA3 for 1 hr at RT, followed by the M13 antibody at 1:500 dilution for another 1 hr at RT. Alexa Fluor 647 or Alexa Fluor 555 conjugated anti-mouse IgG secondary antibodies (Thermo Scientific) were then incubated with the array for 1 hr. After proper wash, slides were scanned at 10 micron resolution using TECAN scanner.

REFERENCES

1. Karthikeyan K, Barker K, Tang Y, Kahn P, Wiktor P, Brunner A, Knabben V, Takulapalli B, Buckner J, Nepom G, LaBaer J, Qiu J. A Contra Capture Protein Array Platform for Studying Post-translationally Modified (PTM) Auto-antigenomes. Mol Cell Proteomics. 2016 July; 15(7):2324-37. doi: 10.1074/mcp.M115.057661. Epub 2016 May 2. PubMed PMID: 27141097; PubMed Central PMCID: PMC4937507.

2. Kay, B. K. et al., eds. Phage display of peptides and proteins: a laboratory manual The following claims are not intended to be limited to the embodiments and other details provided herein.

What is claimed is:

1. A method for affinity selection with arrayed target proteins, comprising the steps of:
    a) providing an array comprising arrayed target proteins, wherein the arrayed target proteins comprise MAP2K5, CTBP1, SARA1A, CDK2 and RPS6KA3;
    b) incubating a phage display material with the array;
    c) washing the array to remove non-binding phage display material from the arrayed target proteins;
    d) eluting from the array any binding phage display material;
    e) amplifying the binding phage display material;
    f) performing at least a further round of affinity selection repeating steps a)-d), whereby performing at least two rounds of affinity selection according to steps a) to d) yields bound phage display material having the highest affinity for at least one of the arrayed target proteins; and
    g) isolating pools of the bound phage display material to identify phage display material having the highest affinity for the at least one of the arrayed target proteins.

2. The method of claim 1, wherein providing an array of step (a) comprises:
    i) transcribing and translating a nucleic acid molecule linked to a solid support, wherein the nucleic acid molecule encodes a fusion protein, the fusion protein comprising a target polypeptide and a first member of a protein binding pair;
    wherein the first member of the protein binding pair binds to a second member of the protein binding pair, wherein the second member of the protein binding pair is linked to the solid support; wherein the arrayed target protein comprises the fusion protein bound to the solid support via the protein binding pair;
    wherein the target polypeptides of the arrayed target proteins comprise MAP2K5, CTBP1, SRA1A, CDK2 and RPS6KA3.

3. The method of claim 1, wherein identifying phage display material having the highest affinity for at least one of the arrayed target proteins comprises analyzing the isolated pools of bound phage display material via macrowell analysis or ELISA.

4. The method of claim 2, wherein the first member of the protein binding pair comprises an antibody epitope, and the second member of the protein binding pair comprises an antibody.

5. The method of claim 4, wherein the first member of the protein binding pair comprises a glutathione S-transferase (GST) epitope and the second member of the protein binding pair comprises an antibody that binds the GST epitope.

6. The method of claim 2, wherein the first member of the protein binding pair comprises a Halo Tag ligand, and the second member of the protein binding pair comprises a Halo Tag.

* * * * *